(12) United States Patent
Weiss

(10) Patent No.: US 6,428,474 B1
(45) Date of Patent: Aug. 6, 2002

(54) SURGICAL INSTRUMENT

(76) Inventor: Sol Weiss, 17144 Bullock St., Encino, CA (US) 91316

( * ) Notice: Subject to any disclaimer, the term of this patent is extended or adjusted under 35 U.S.C. 154(b) by 0 days.

(21) Appl. No.: 09/578,016

(22) Filed: May 24, 2000

(51) Int. Cl.$^7$ ................................................. A61B 1/32
(52) U.S. Cl. ..................................... 600/224; 600/220
(58) Field of Search ................................ 600/220, 224, 600/225, 222

(56) References Cited

U.S. PATENT DOCUMENTS

| | | | | |
|---|---|---|---|---|
| 2,083,573 A | * | 6/1937 | Morgan | 600/224 |
| 2,954,025 A | * | 9/1960 | Grieshaber | 600/220 |
| 4,597,382 A | * | 7/1986 | Perez, Jr. | 600/220 |
| 5,081,983 A | * | 1/1992 | Villalta et al. | 600/224 |
| 5,868,668 A | * | 2/1999 | Wieiss | 600/224 |
| 6,024,696 A | * | 2/2000 | Hoffman | 600/224 |

* cited by examiner

Primary Examiner—Paul J. Hirsch
(74) Attorney, Agent, or Firm—Gerald L. Price

(57) ABSTRACT

A surgical instrument for spreading apart openings of natural orifices or surgically made openings to perform procedures on internal structures and/or organs of a patient. The instrument includes a pair of upper and lower blades that open to spread apart the area being examined so that a surgical tool can be inserted therein. A second pair of lateral blades are fixedly mounted between the spaced pair of upper and lower blades. The instruments can be eliminated from the area of view by allowing the surgical tool to pass up into a gate while maintaining the spread-apart condition of the area being examined. The blades can then be restored to their closed position after the tool is withdrawn. The gate may have a plurality of notches for accommodating differing surgical tools.

8 Claims, 5 Drawing Sheets

SURGICAL INSTRUMENT

BACKGROUND OF THE INVENTION

1. Field of the Invention

The invention relates to surgical instruments; and, more particularly, to diagnostic and surgical instruments for use in abdominal, thoracic or vaginal and anal surgical procedures that may also include endoscopies.

2. Related Art

Certain surgical and diagnostic devices are known for examining vaginal and other cavities. For example, women of a certain age should have a diagnostic pap smear annually. Certain prior art devices, known as speculums, are used which consist of a pair of wide or broad blades, but such are uncomfortable to the patient, causing much discomfort.

Also, when such instruments are used in examining a body cavity, such as the vagina, a second instrument is inserted into the vagina through the speculum. Such an instrument is called a lateral vaginal retractor and is used to retract the vaginal side walls which normally obstruct the doctor's view into the patient's cervix. During a surgical procedure, the surgeon needs to insert a clamp, a source of lighting, a suctioning catheter, and irrigation tube through the speculum, thus further obstructing the surgeon's view of the cervix which might interfere with the surgical procedure being performed.

In my U.S. Pat. No. 5,868,668, the teachings of which are incorporated herein by reference, I disclose a surgical and diagnostic instrument which eliminates the need for a lateral vaginal retractor during vaginal surgery. The instrument should be anatomically designed with a narrow oval shape in its closed position to allow it to be inserted comfortably into the patient's vagina without the discomfort generally associated with a conventional speculum. It allows the introduction of other instruments such as a light, an irrigation tube, etc. without obstruction the surgeon's view.

I have found that, although this instrument in my U.S. Pat. No. 5,868,668 works quite well, it is not necessary that the blades 21, 22 disclosed therein are part of the pivoting mechanism. By making these blades integral the upper flange assembly, I reduce the number of parts and need for careful machining of these blades.

SUMMARY OF THE INVENTION

It is an object of this invention to provide an improved surgical and diagnostic instrument for examining a patient's body cavity, such as a vagina, eliminating the need for a lateral vagina retractor during surgery.

It is another object of this invention to carry out the foregoing object that is anatomically designed (four quadrant retraction allows the blades to be of less width producing a narrower instrumentation) to cause little if any discomfort to the patient.

It is still another object of this invention to provide a multi-bladed vaginal diagnostic and surgical instrument which is quickly and easily activated to expand the blades with slight rotation movement and little discomfort to the patient.

It is further an object of this invention to carry out the foregoing objects allowing easy insertion into the body cavity being examined without allowing the instrument to slip out of the body cavity during examination.

Such an instrument should allow a tenaculum and other diagnostic tools to be moved out of the area of view of the surgeon while carrying out diagnostic procedures.

These and other objects are preferably accomplished by providing a surgical instrument for spreading apart openings of natural orifices or surgically made openings to perform procedures on internal structures and/or organs of a patient. The instrument includes a plurality of spaced upper and lower blades that open to spread apart the area being examined so that a surgical tool can be inserted therein. A second pair of lateral blades are fixedly mounted between the spaced pair of upper and lower blades. The instrument can be eliminated from the area of view by allowing the surgical tool to pass up into a gate while maintaining the spread-apart condition of the area being examined. The blades can then be restored to their closed position after the tool is withdrawn. The gate may have a plurality of notches for accommodating differing surgical tools.

DESCRIPTION OF THE PREFERRED EMBODIMENT

Figure 1:
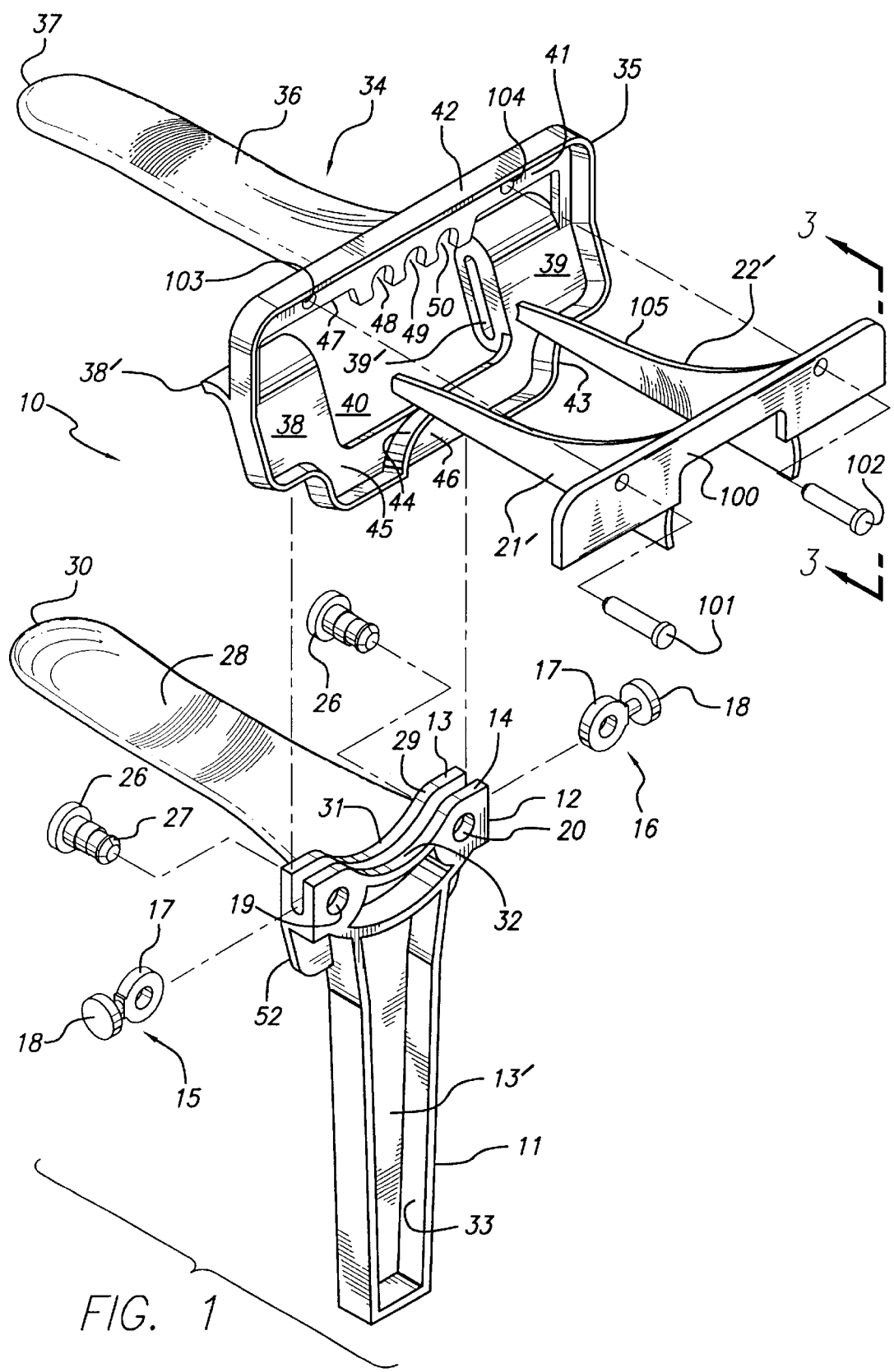
FIG. 1 is an exploded view of a surgical instrument in accordance with the teachings of the invention.

Referring now to FIG. 1, a surgical instrument 10 is shown having a handle 11 and an integral flanged portion 12 comprised of a pair of spaced flange 13, 14 and a planar midsection 13'. A pair of knob and washer combinations 15, 16 are provided, each having an integral washer portion 17 and an integral knob portion 18. These combinations 15, 16 are adapted to be inserted between flanges 13, 14 aligned with apertures 19, 20, respectively (aligned apertures similar to 19, 20 are disposed in flange 13 and are not visible in FIG. 1).

A boss 26 having a stepped 3-part pin 27 integral with each boss 26 extends toward apertures 19, 20.

In my U.S. Pat. No. 5,868,668, the teachings of which are incorporated herein by reference, blades 21, 22 each included an outwardly extending blade portion 24. These blade portions have been eliminated in this application and are now part of the upper apparatus of my invention as shown in FIG. 1, and will be discussed. However, the pivoted connection and operation of boss 26, pin 27, and combinations 15, 16, is identical to that of the blades 21, 22 in my U.S. Pat. No. 5,868,668.

Thus, referring again to FIG. 1, a blade 28, slightly curved in cross-section, is integral with flange 13 and extends outwardly therefrom in a plane generally normal to the plane of handle 11 below the upper edge 29 of flange 13. Blade 28, at its forward end 30, is curved and depressed areas 31, 32 are provided in the middle of the upper edges of flanges 13, 14. The handle 11 may have a hollowed out interior 33 to save weight and costs of manufacture.

A blade assembly 34 is provided having a main body portion 35 and an integral fourth blade 36 extending therefrom lying in a plane generally normal to the plane of the main body portion 35. Blade 36 terminates at its forward end 37 in a curved end and is also slightly curved in cross-section.

Main body portion 35 is adapted to fit over flanged portion 12 (FIG. 2) and is generally rectangular with a pair of spaced inner curved walls 38, 39 flanged at top (see flange 41' in FIG. 1) forming a space 40 therebetween formed between upper rail 42 of main body portion 35 and the lower rail 43 thereof. An oval opening or slot 39' is formed integral with each curved wall 38, 39. Rail 43 has a raised flange portion 44 at generally the middle thereof and walls 38, 39 are interconnected by an inner partition wall 45. Walls 38, 39 are curved at their upper ends. A portion 46 of wall 45 is thus accessible below flange portion 44 to provide a thumb rest for instrument 10 as will be discussed.

Rail 42 includes a downwardly depending elongated flange 47 having a plurality of spaced notches 48 to 50 for reasons to be discussed. Although shown as grooves, tracks, or notches, notches 48 to 50 can have a variety of configurations.

Figure 3:
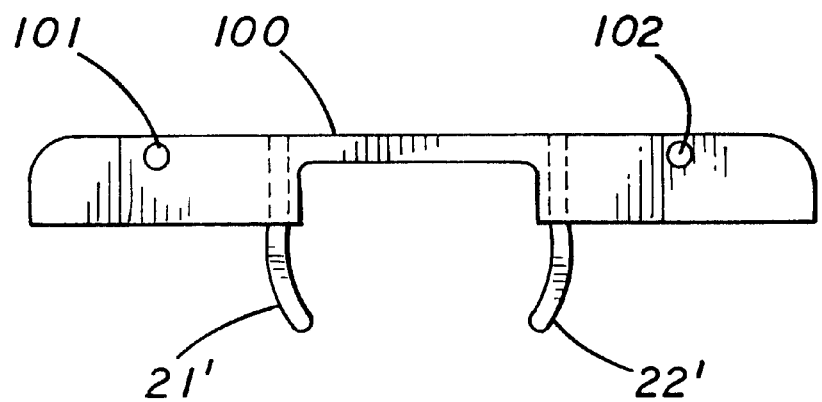
FIG. 3 is a view taken along lines 3—3 of FIG. 1, parts thereof being omitted for convenience of illustration.
Figure 4:
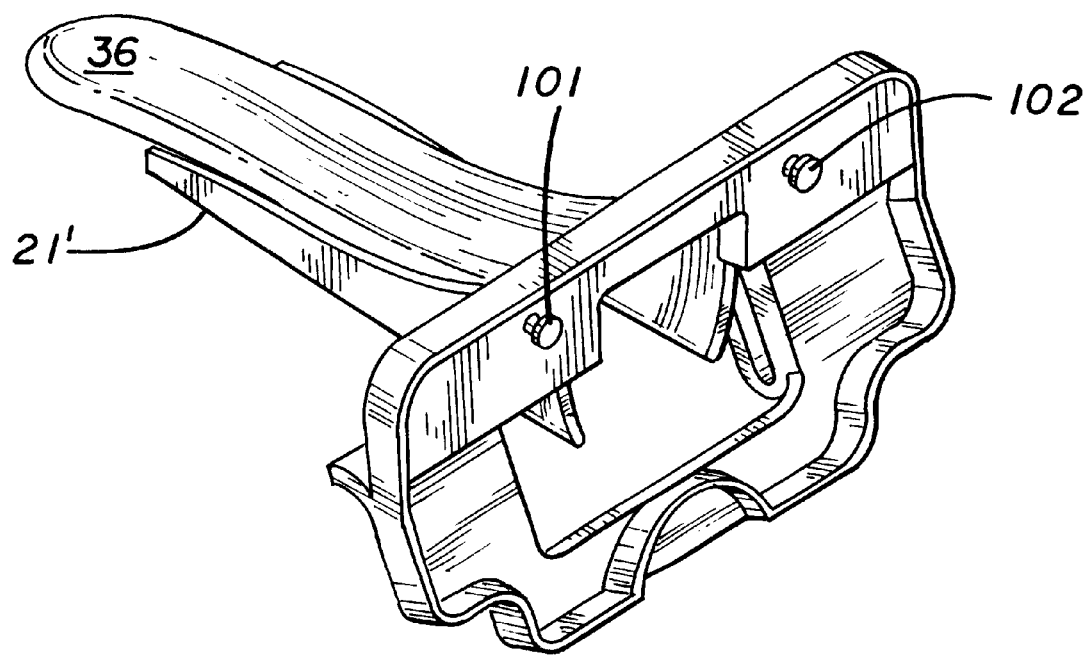
FIG. 4 is a perspective view of the upper blade assembly alone of the instrument of FIG. 1.
Figure 5:
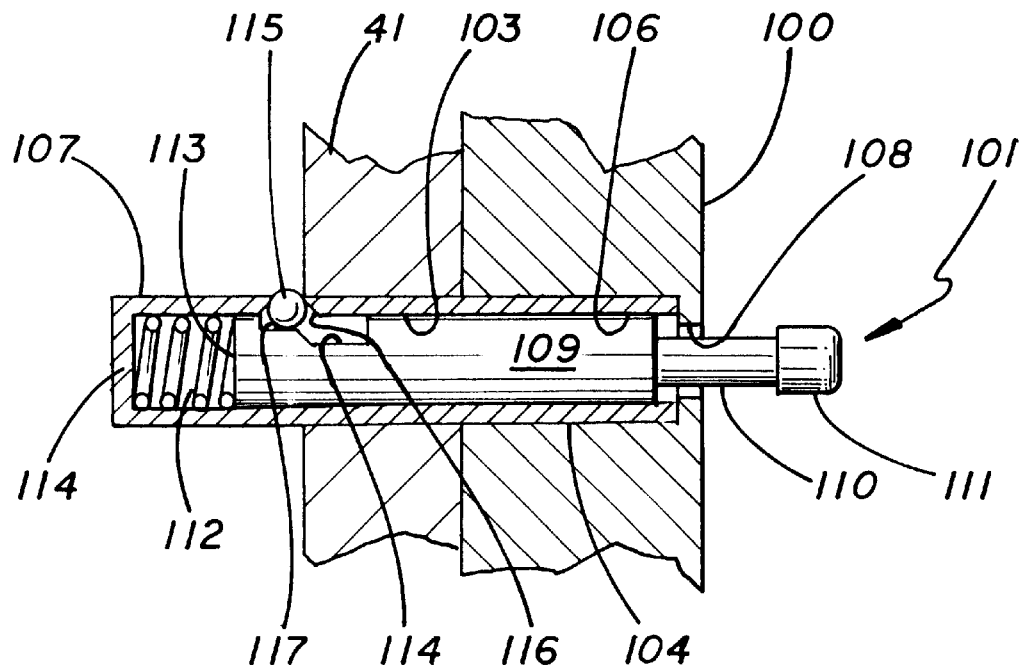
FIG. 5 is a view taken along lines 5—5 of FIG. 6.

As heretofore discussed, in my U.S. Pat. No. 5,868,668, blades 21, 22 were part of the handle 11. However, in this improved invention, blades 21', 22' (see also FIG. 3) are integrally mounted to a flange 100 having a pair of spaced pins 101, 102 adapted to be received in aligned apertures 103, 104, respectively, in blade assembly 34. Each blade 21', 22' is arcuate in cross-section, as can be seen in FIG. 3, is shorter than blades 28, 36 (see FIG. 2) and disposed therebetween. Each blade 21', 22' is tapered on its upper surface as seen at taper 105 in FIG. 1. The final assembly of blades 21', 22' to blade assembly 34 is shown in FIG. 4. The forward ends of blades 21", 22' may curve inwardly toward each other from the plane of blades 21,', 22'. As seen in FIG. 5, flange 100 has a pair of throughbores 106 (only one visible in FIG. 5) aligned with holes 103, 104, respectively. A hollow cylindrical element 107 is mounted in each throughbore 106 with a reduced diameter opening 108 in flange 100 leading into throughbore 106. Each pin 101 includes a piston 109 reciprocal in each throughbore 106, and generally conforming to the inner diameter of element 107, with a reduced diameter piston shaft 110 integral with enlarged head 111. A coiled spring 112 is disposed between the forward end 113 of piston 109 and the forward end wall 114 of element 107. A ball element 115 is adapted to extend out of opening 116 in element 107 and peened thereabout to trap ball element 115 so it can't extend out of opening 116. A first reduced diameter section 117 is provided in piston 109 leading to a second reduced diameter section 118, greater in diameter, in piston 109. In this manner, pushing in on head 111 against the bias of spring 112 allows ball element 115 to fall into reduced diameter section 118 allowing flange 100 and interconnected blades 21', 22' to be withdrawn from blade assembly 34. Flange 100 can be quickly and easily assembled to blade assembly 34 by inserting cylindrical elements 107 into aligned holes 103, 104 to snap ball elements 115, now in reduced diameter section 117, out of holes 116 when ball elements 115 move past flange 111 and snap out of holes 116 as seen in FIG. 5.

The final assembly of flange 100, and blades 21', 22', is shown in FIG. 4.

Figure 2:
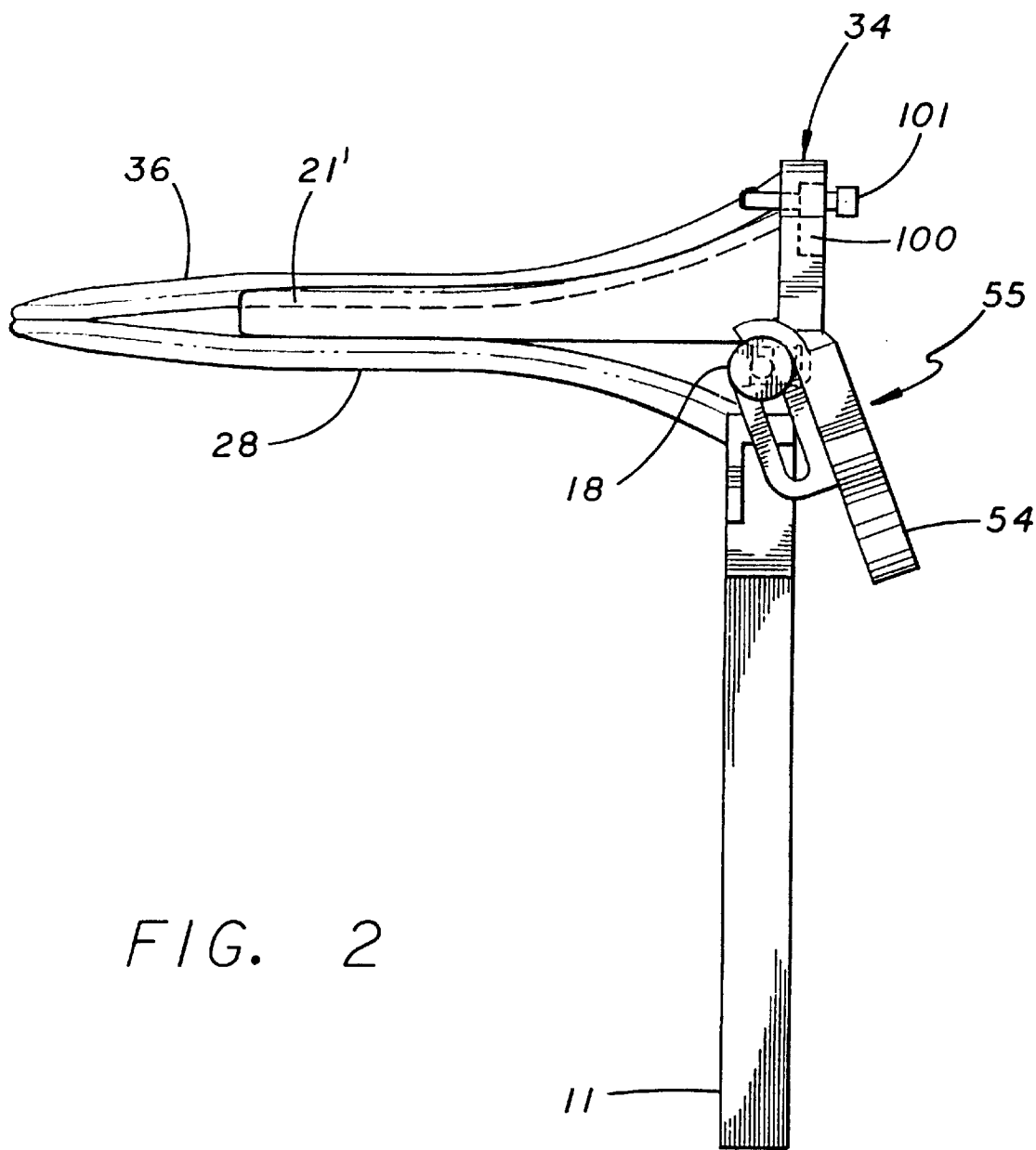
FIG. 2 is a side view of the assembled surgical instrument of FIG. 1, the blades being in closed position.

It can be seen by comparing FIGS. 1 and 2 that the main housing portion 35 of blade assembly 34 is mounted over flanged portion 12 as described in my U.S. Pat. No. 5,868,668.

Figure 6:
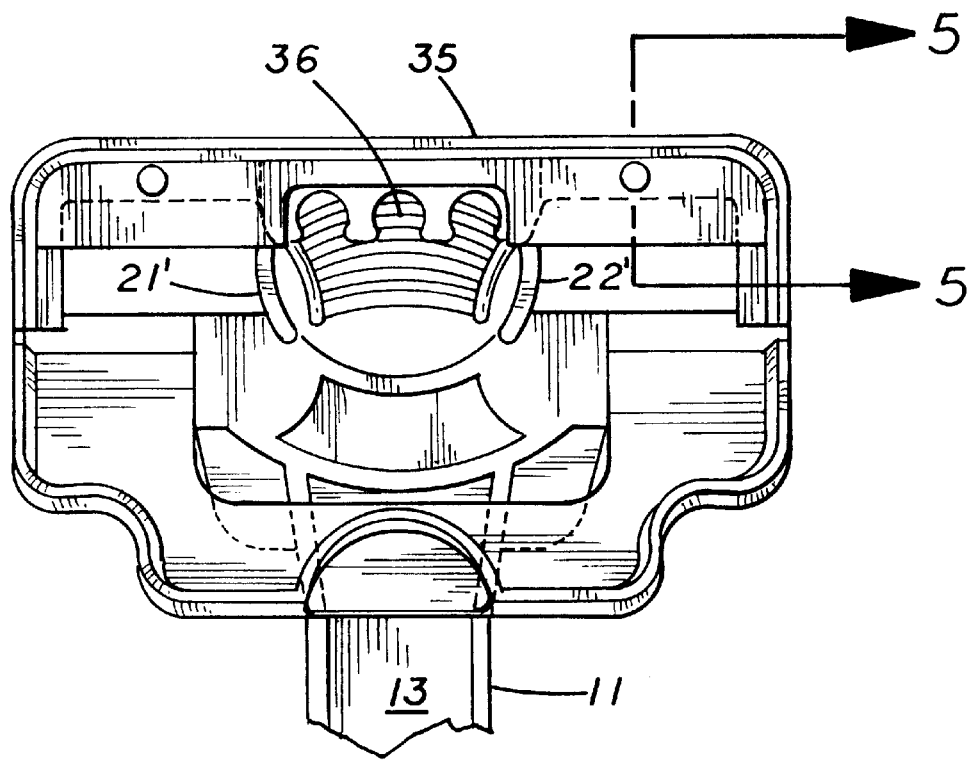
FIG. 6 is a rear view of the instrument of FIG. 2, the blades being in closed position.

The washer portions 17 of combinations 15, 16 are inserted between spaced flanges 13, 14. Stepped pins 27 are now inserted into the respective aligned apertures 19, 20 with levers 23 extending out of slot 39' (see FIG. 6) and thus accessible outside of blade assembly 34.

As seen in FIG. 2, the flanged portion 12 is at an angle with respect to handle 11 so that knobs 18 are retained within slots 39'. The lower portions 54 of main housing portion 35 is also angled as seen in FIG. 2.

Figure 7:
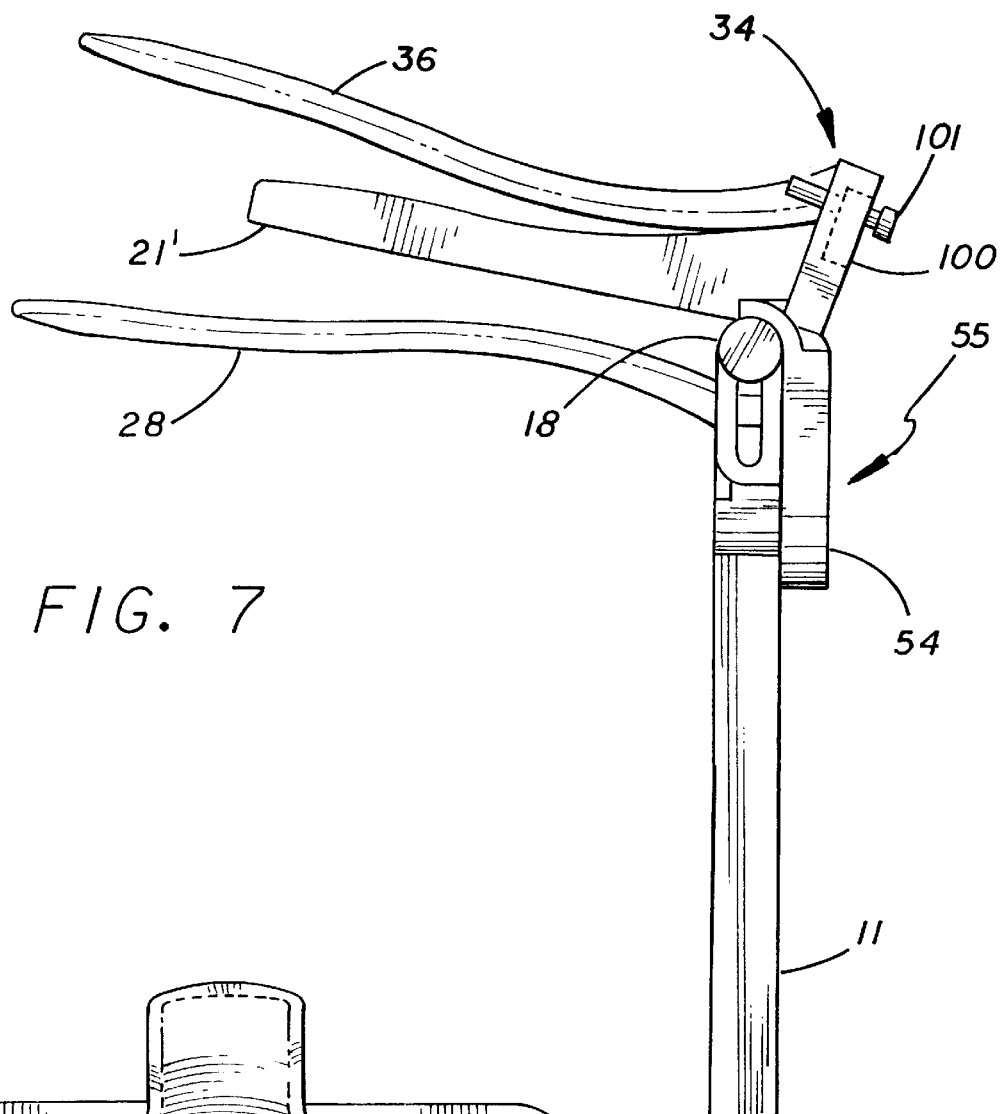
FIG. 7 is a view similar to FIG. 2 showing the blades in open position.
Figure 8:
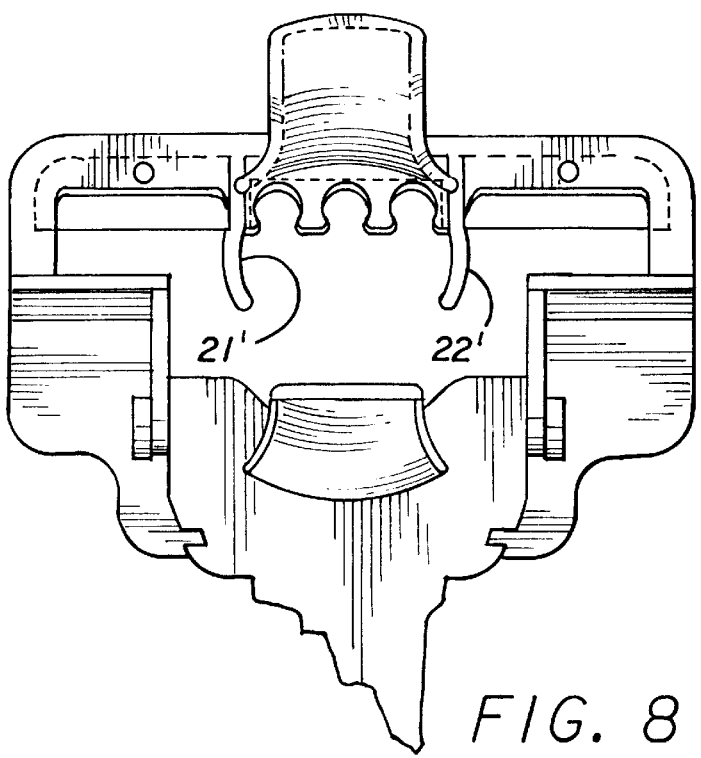
FIG. 8 is a view similar to FIG. 6 showing the blades in open position.

In operation, as seen in FIG. 7, pushing it at thumb rest 46 (not visible in FIG. 5—see FIG. 1) on lower portion 54 in the direction of arrow 55 raises blade 36. Continuing to push up on thumb rest 46 in the direction of arrow 55 raises blades 36, 21', and 22' further with knob 18 moving down slot 39'.

Pins 27 are stepped or not perfectly round such as having a non-round or spiraled midsection, as midsection 100 in my U.S. Pat. No. 5,868,668, so that, when the arms 23 are rotated downwardly, knobs 18 are pulled inwardly tightening the assembly 23.

The operation of instrument 10 is discussed in detail in my U.S. Pat. No. 5,868,668. Instrument 10 has a narrow oval configuration as instrument 10 in U.S. Pat. No. 5,868,668. A conventional tenaculum can be inserted between the pin blades, when in the FIG. 7 position, as discussed in my patent. Notches 48 to 50 are used in the same manner as disclosed in my patent.

My instrument is of a simple construction requiring no moving parts. It is a separate and distinct tool that can be made, adapted, and attached for speculums or other surgical instruments. It can be made of metal, plastic, and coated (plastic or laser coating) for regular, electrocautery, or laser usage. It is a separate and distinct tool that can be attached to speculums or other surgical instruments in order to prevent other tissues (retraction) from cascading into the site of surgery or other procedures.

My instrument is a separate and distinct tool that can be attached to speculums or other surgical instruments in order to present laterally, without extending beyond the parameters of the original instrumentation (vertical blades), which would become unduly uncomfortable for the patient or hamper the operator. It is a separate and distinct tool that can be attached to speculums or other surgical instruments in order to provide assistant usage or be easily removed if not needed (portability). It is a separate and distinct tool that can be attached to speculums or other surgical instruments providing a lever for the finger or fingers to shift the yoke into an elevated or lower position as desired. My instrument is a separate and distinct tool that can be attached to speculums or other surgical instruments that acts harmoniously with the part or parts of the speculum until it can be fixed in an optimal position. It is a separate and distinct tool that can be attached to speculums or other surgical instruments that can be used in conjunction with many diagnostic and/or therapeutic uses. It is a separate and distinct tool that can be attached to speculums or other surgical instruments that remains locked in place to prevent slippage during surgical and diagnostic procedures by numerous interlocking tabs.

My instrument is a separate and distinct tool that can be attached to speculums or other surgical instruments that have the lateral blades conform to the contours of the vertical blades to avoid obstructing vertical blades from assuming the closed position or projecting away from the vertical blades that penetration of the vaginal vault or other similar applications would be jeopardized. It is a separate and distinct tool that can be attached to speculums or other surgical instruments that have such simplicity in design that it allows for low cost in manufacturing and marketing in a budgetary conscious public. It is a separate and distinct tool that can be attached to speculums or other surgical instruments that wrap around the yoke or poles of the instruments so as to be reinforced from bending inwards yet persist in its retraction of tissues.

I have disclosed a separate and distinct tool that can be attached to speculums or other surgical instruments that have inwardly bent and rounded edges of their tips to avoid snagging tissues.

There is thus disclosed a surgical instrument which is a four-way spreader useful in examining the body of a patient. The spreader holds open the area one desires to examine, such as the vaginal pouch leading to the uterus, and can be moved quickly and easily off to the side upon insertion of a conventional diagnostic tool, such as a tenaculum, to provide better visibility and maneuverability. The instrument can be made of any suitable materials, such as plastic.

I claim:

1. In a surgical instrument for carrying out diagnostic and therapeutic procedures on the interior organs of the human body comprising a handle having a pair of integral spaced flanges at the upper end thereof, said spaced flanges having a pair of spaced apertures therethrough, and a first blade fixed to said flanges extending outwardly therefrom, a flange housing mounted to said spaced flanges also having a second blade fixed thereto and extending outwardly spaced from and above said first blade said flange housing being pivotally connected to said handle and having an opening therethrough for receiving a surgical instrument therethrough, the improvement which comprises:

a pair of blades mounted to said flange housing extending outwardly therefrom and between said first and second blades on opposite sides thereof.

2. The instrument of claim 1 wherein said pair of blades extend from a flange assembly removable from said flange housing.

3. The instrument of claim 2 wherein said flange assembly snap fits onto said flange housing.

4. The instrument of claim 3 wherein said flange assembly is spring biased into engagement with said flange housing.

5. The instrument of claim 1 wherein said pair of blades are concave in cross-section.

6. The instrument of claim 5 wherein the pair of blade s are curved inwardly toward each other.

7. The instrument of claim 1 wherein said pair of blades are tapered on their upper surfaces from their terminal ends thereof upwardly and inwardly toward said flange housing.

8. The instrument of claim 1 wherein each of said first and second blades is elongated having a pair of spaced elongated sides and curved, said pair of blades being disposed inwardly of the elongated curved sides of said first and second blades.

* * * * *